United States Patent
Wei

(10) Patent No.: US 9,658,218 B2
(45) Date of Patent: May 23, 2017

(54) DETERMINATION OF TOTAL ANALYTE CONCENTRATION

(75) Inventor: Tie Quan Wei, Wilmington, DE (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 412 days.

(21) Appl. No.: 13/465,574

(22) Filed: May 7, 2012

(65) Prior Publication Data

US 2013/0295592 A1    Nov. 7, 2013

(51) Int. Cl.
| | |
|---|---|
| G01N 33/566 | (2006.01) |
| G01N 33/53 | (2006.01) |
| G01N 21/76 | (2006.01) |
| G01N 21/64 | (2006.01) |
| G01N 33/94 | (2006.01) |
| G06F 19/24 | (2011.01) |

(52) U.S. Cl.
CPC ..... *G01N 33/5306* (2013.01); *G01N 21/6428* (2013.01); *G01N 21/76* (2013.01); *G01N 33/9493* (2013.01); *G06F 19/24* (2013.01)

(58) Field of Classification Search
CPC .......... G01N 21/6428; G01N 33/5306; G01N 21/76; G06F 19/24
USPC ........................................................ 436/501
See application file for complete search history.

(56) References Cited

U.S. PATENT DOCUMENTS

| | | | |
|---|---|---|---|
| 5,698,448 A | 12/1997 | Soldin | |
| 5,780,307 A | 7/1998 | Soldin | |
| 6,187,547 B1 | 2/2001 | Legay et al. | |
| 2005/0112778 A1* | 5/2005 | Wang | C07D 498/18 436/501 |
| 2006/0246435 A1 | 11/2006 | Kempin et al. | |
| 2008/0108147 A1 | 5/2008 | Wei et al. | |
| 2011/0136136 A1 | 6/2011 | Wei et al. | |
| 2011/0318754 A1 | 12/2011 | Wei | |

FOREIGN PATENT DOCUMENTS

| | | |
|---|---|---|
| EP | 0152603 A1 | 8/1985 |
| WO | 9117439 A1 | 11/1991 |
| WO | 9507468 A1 | 3/1995 |

OTHER PUBLICATIONS

European Search Report and Search Opinion of European Application No. 13787140.6 dated Dec. 22, 2015.
International Search Report for International Application PCT/US2013/039810 Dated Sep. 20, 2013.

* cited by examiner

*Primary Examiner* — Chris L Chin
(74) *Attorney, Agent, or Firm* — Theodore J. Leitereg

(57) ABSTRACT

Methods and reagents are disclosed for determining a total amount of an analyte in an unknown sample suspected of containing the analyte in the presence of endogenous interfering substances. The methods involve measuring an amount [Y] of the portion of the analyte in the unknown sample that is bound by endogenous binding substances employing an assay for the analyte. An amount [Z] of analyte in the unknown sample that is not bound by endogenous binding substances is determined by the formula: [Z]=a[Y]+b, wherein "a" and "b" are predetermined by conducting the assay on samples containing known amounts of the analyte but substantially free from endogenous interfering substances. Adding [Y] and [Z] yields the total amount [X] of the analyte in the unknown sample.

20 Claims, 1 Drawing Sheet

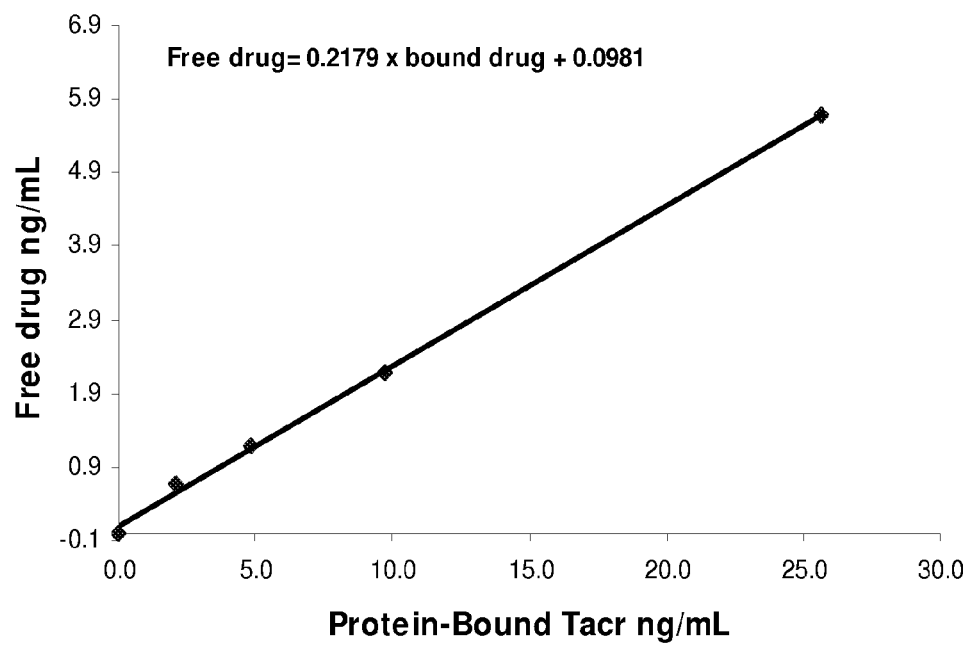

DETERMINATION OF TOTAL ANALYTE CONCENTRATION

BACKGROUND

The invention relates to methods and kits for the determination of the concentration of an analyte in a sample suspected of containing the analyte. More particularly, the invention relates to determining analyte concentration in unknown samples in the presence of interfering substances that participate in the generation of false signals in the format of conventional immunoassays.

The body relies upon a complex immune response system to distinguish self from non-self. At times, the body's immune system must be controlled in order to either augment a deficient response or suppress an excessive response. For example, when organs such as kidney, heart, heart-lung, bone marrow and liver are transplanted in humans, the body will often reject the transplanted tissue by a process referred to as allograft rejection.

In treating allograft rejection, the immune system is frequently suppressed in a controlled manner with drug therapy. Immunosuppressant drugs are carefully administered to transplant recipients in order to help prevent allograft rejection of non-self tissue. Two most commonly administered immunosuppressive drugs to prevent organ rejection in transplant patients are Cyclosporine (CSA) and FK-506 (FK or tacrolimus). Another drug that finds use as an immunosuppressant in the United States and other countries is sirolimus, also known as rapamycin. Derivatives of sirolimus are also said to be useful as immunosuppressants. Such derivatives include, for example, Everolimus, and the like.

The side effects associated with some immunosuppressant drugs can be controlled in part by carefully controlling the level of the drug present in a patient. Therapeutic monitoring of concentrations of immunosuppressant drugs and related drugs in blood is required to optimize dosing regimes to ensure maximal immunosuppression with minimal toxicity. Although immunosuppressant drugs are highly effective immunosuppressive agents, their use must be carefully managed because the effective dose range is often narrow and excessive dosage can result in serious side effects. On the other hand, too little dosage of an immunosuppressant can lead to tissue rejection. Because the distribution and metabolism of an immunosuppressant drug can vary greatly between patients and because of the wide range and severity of adverse reactions, accurate monitoring of the drug level is essential.

In therapeutic drug monitoring field, selectively detecting the parent drug over its metabolites is often an important goal for designing immunoassays. This is especially true for immunosuppressant drugs. For that reason, HPLC tandem MS assays have become standard methods for the measurement of sirolimus, tacrolimus and other immunosuppressant drugs due to their ability to selectively measure the parent drug. However, the above methods are costly and time-consuming and are often employed to verify positive results obtained by another assay method rather than used in laboratories as an initial determination.

Many whole blood assays for immunosuppressant drugs require a manual step using reagents to extract the drug from blood constituents. The drug molecules and drug metabolite molecules are dissociated from endogeneous binding proteins and are extracted into a relatively clean solution in which plasma proteins and lipoprotein particles as well as most other molecules are removed. Because precipitation techniques are usually used, the extracted sample is basically free of most blood macromolecules including one or both of binding proteins for the immunoassay components and other substances that may interfere with the assay signal. Thus, in the extracted samples, the parent drug and its metabolites are dissolved as unbound, individual molecules and compete with one another for reaction with an assay antibody in the immunoreaction mixture. The binding of assay antibody to the drug occurs in the absence of most endogenous binding substances in these assays. The cross-reactivity of a drug metabolite depends mostly on its antibody binding affinity in such assays.

In a homogeneous assay for an immunosuppressant drug where there is no manual extraction or separation of the drug from blood constituents, an antibody for the immunosuppressant drug has to detect the drug in the presence of most or all blood constituents, the presence of which might interfere in the assay result such as, for example, by with the antibody to the immunosuppressant drug, thus leading to a false assay result or interfering with a measurement of true drug concentration in the blood sample.

There is, therefore, a continuing need to develop fast and accurate diagnostic methods to measure levels of analytes in samples taken from a patient. The methods should be fully automatable and be accurate even when conducted on samples having various interfering substances. The assay should provide an accurate measurement of the amount of the analyte in the sample while minimizing inaccuracies resulting from interfering substances, particularly non-specific interfering substances, present in a sample.

SUMMARY

Some examples in accordance with the principles described herein are directed to methods of determining a total amount of an analyte in an unknown sample suspected of containing the analyte in the presence of endogeneous interfering substances potentially present in the unknown sample. The methods involve measuring an amount [Y] of the portion of the analyte in the unknown sample that is bound by endogenous binding substances (bound analyte) employing an assay for the analyte. An amount [Z] of analyte in the unknown sample that is not bound by endogeneous binding substances (free analyte) is determined by the formula: $[Z]=a[Y]+b$, wherein "a" and "b" are predetermined by conducting the assay on samples containing known amounts of the analyte but substantially free from endogenous interference interfering substances. Adding [Y] (bound analyte) and [Z] (free analyte) yields a total amount [X] of the analyte in the unknown sample.

Some examples in accordance with the principles described herein are directed to methods of determining a total amount of tacrolimus in an unknown sample suspected of containing tacrolimus in the presence of endogeneous interfering substances potentially present in the unknown sample. An amount [Y] of the portion of tacrolimus that is bound by endogenous binding substances is measured by determining an amount [V] of tacrolimus by means of an assay conducted on a portion of the sample in the presence of an agent capable of displacing tacrolimus from endogeneous binding substances, determining an amount [W] of tacrolimus by means of an assay conducted on a portion of the sample in the absence of the agent capable of displacing tacrolimus from endogeneous binding substances, and subtracting [W] from [V]. An amount [Z] of tacrolimus that is not bound by endogeneous binding substances is determined by the formula: $[Z]=a[Y]+b$, wherein "a" and "b" are predetermined by conducting the assay on samples containing known amounts of the tacrolimus analyte but substantially free from endogenous interfering substances. In the above equation, "a" is the slope of a regression between the analyte that is not bound by endogenous binding substances and the analyte that is bound by endogenous binding substances and "b" is the intercept of the regression. The total amount [X] of tacrolimus in the unknown sample is determined by adding [Y] and [Z].

BRIEF DESCRIPTION OF THE DRAWINGS

FIG. 1 is a plot of a concentration of free tacrolimus against a concentration of tacrolimus that is bound by endogenous binding substances.

DETAILED DESCRIPTION OF SPECIFIC EMBODIMENTS

General Discussion

Examples in accordance with the principles described herein are directed to the accurate measurement of a total amount of an analyte in an unknown sample that potentially contains endogenous interfering substances. Although samples may be treated with a displacing agent to displace analyte in an unknown sample from any endogenous binding substances that may be present, endogenous interfering substances such as, for example, non-specific interfering proteins that may be present in the unknown sample, bind to immunoassay components and result in an inaccurate determination of analyte concentration in the unknown sample. Furthermore, many unknown samples do not have endogenous substances that interfere with an assay signal; however, for those unknown samples that do have such substances, the amounts of such endogenous interfering substances vary from sample to sample. In accordance with the principles described herein, true analyte concentration may be measured in unknown samples in the presence of endogenous interfering substances such as, for example, non-specific interfering proteins.

In accordance with the principles described herein, a relationship between analyte that is bound by endogenous binding substances (hereinafter referred to as "bound analyte") and analyte that is not bound by endogenous binding substances (hereinafter referred to as "free analyte") in known samples that are substantially free from endogenous interfering substances is established to determine a set of coefficients, which may then be employed to determine true analyte concentration in unknown samples in the presence of endogenous interfering substances that may be present therein. Samples containing known amounts of analyte that are substantially free from endogenous interfering substances such as, for example, binding proteins, are subjected to an assay for the analyte to determine a relationship between bound analyte and free analyte and the resulting data is subjected to regression analysis. The amount of free analyte is plotted against the amount of bound analyte for the known samples to obtain coefficients that can be employed to calculate, for samples containing an unknown amount of analyte and potentially containing endogenous interfering substances, the true total amount analyte in the unknown samples. The relationship between free analyte and bound analyte that is established for a particular assay and reagents using the samples of known concentration may be employed to determine true analyte concentration for samples of unknown analyte concentration even though such samples may contain endogenous interfering substances such as, for example, non-specific interfering proteins.

The sample to be tested may be non-biological or biological. "Non-biological samples" are those that do not relate to a biological material and include, for example, soil samples, water samples, air samples, samples of other gases and mineral samples. The phrase "biological sample" refers to any biological material such as, for example, body fluid, body tissue, body compounds and culture media. The sample may be a solid, semi-solid or a fluid (a liquid or a gas) from any source. In some embodiments the sample may be a body excretion, a body aspirant, a body excisant or a body extractant. The body is usually that of a mammal and in some embodiments the body is a human body. Body excretions are those substances that are excreted from a body (although they also may be obtained by excision or extraction) such as, for example, urine, feces, stool, vaginal mucus, semen, tears, breath, sweat, blister fluid and inflammatory exudates. Body excisants are those materials that are excised from a body such as, for example, skin, hair and tissue samples including biopsies from organs and other body parts. Body aspirants are those materials that are aspirated from a body such as, for example, mucus, saliva and sputum. Body extractants are those materials that are extracted from a body such as, for example, whole blood, plasma, serum, spinal fluid, cerebral spinal fluid, lymphatic fluid, synovial fluid and peritoneal fluid.

The analyte is a substance of interest or the compound or composition to be detected and/or quantitated. Analytes include, by way of illustration and not limitation, therapeutic drugs, drugs of abuse, metabolites, pesticides, volatile organic compounds, semi-volatile organic compounds, non-volatile organic compounds, proteins, polysaccharides, pollutants, toxins, lipids and nucleic acids, (DNA, RNA), for example.

Examples in accordance with the principles described herein have particular application to analytes that are in samples containing endogenous substances that bind to the analyte. Such endogenous binding substances are those that are present in a sample taken from its source. The nature of the endogenous binding substances is dependent on one or more of the nature of the sample, the nature of the source of the sample, the nature of the analyte, and the nature of a molecular complex comprising the analyte, for example. The endogenous binding substances may be both endogeneous binding substances and endogenous interfering substances.

Endogenous binding substances are those from which analyte may be displaced by a displacing agent as discussed hereinbelow. Endogenous binding substances include both endogenous specific binding substances and endogenous non-specific binding substances. Specific binding substances are substances that have an area on a surface or in a cavity, which specifically binds to and is thereby defined as complementary with, a particular spatial and polar organization of the analyte or vice versa. Specific binding is distinguished from non-specific binding because specific binding involves the specific recognition of one of two different molecules for the other compared to substantially less recognition of other molecules. Non-specific binding substances are substances that bind to an analyte, in general, by means of non-covalent binding between molecules that is relatively independent of specific surface structures. Endogenous binding substances for an analyte include, but are not limited to, proteins that specifically bind to an analyte such as, for example, anti-analyte antibodies and receptors (e.g., immunoglobulins); and immunophilins that are composed of major (e.g., cyclophilin that binds CsA, FK-binding proteins that bind tacrolimus and sirolimus) and minor categories. The minor category contains two groups: one with peptidylprolyl cis/trans isomerase activity (12, 25 and 56-50 kDa, the other without peptidylprolyl cis/trans isomerase activity (14, 37, and 52 kDa), target of rapamycin (TOR); α1 acid glycoprotein, lipoproteins, albumin and globulins; for example, or a combination of two or more of the above.

Interfering substances include any substance that interferes with the production of signal in an assay. Interference may result from the binding of the interfering substance to one or more components of an assay. Such assay components include, but are not limited to, assay antibodies, signal enzymes, linkers, proteins or other reagents that are present on a solid support, and assay reagent substrates, for example. Interfering substances may be, but are not limited to, non-specific binding proteins, for example. As mentioned above, non-specific binding refers to non-covalent binding between molecules that is relatively independent of specific surface structures. Interferences such as non-specific binding may result from several factors including hydrophobic interactions between molecules. The nature of the molecule or molecules that result in interferences such as non-specific binding in assays is dependent on one or more of the nature of the sample and the nature of the immunoassay components, for example. Interfering substances such as non-specific binding proteins are those from which analyte is not displaced by a displacing agent as discussed hereinbelow.

In some examples, interfering substances include, but are not limited to, protein materials such as, for example, non-specific immunoglobulins, substances that may cause reagent agglutination; substances may increase or decrease activity of the signal enzyme or signal molecule in an assay such as, for example, substances such as, e.g., antibodies, that bind to signal-producing enzymes (for example, conversion from enzyme substrate, e.g., chlorophenol red (CPR), to a colored product, e.g., chlorophenol red-β-D-galactopyranoside CPRG); substances that decrease or increase assay antibody binding to an analyte analog present on a solid support; substances that bind to a signal conjugate reagent such as, e.g., a conjugate of an antibody and an enzyme (enzyme-antibody conjugate), which include substances that bind to one or more component parts of the enzyme-antibody conjugate such as, for example, a linking group linking the antibody and the enzyme, the antibody itself, the enzyme itself, or a combination of one or more thereof; substances that may reduce or increase the binding of antibody to the analyte; substances that may change the enzymatic conversion of a substrate to a product for the production of an assay signal, for example, lipophilic materials such as, for example, lipoproteins (e.g., cholesterol and triglyceride), lipid bilayer and plasma membranes; cells such as, for example, red blood cells; for example, or a combination of two or more of the above.

Immunosuppressant drugs are one group of analytes that is susceptible to being bound by endogenous binding substances. As mentioned above, immunosuppressant drugs are therapeutic drugs that are administered to transplant recipients in order to help prevent allograft rejection of non-self tissue. Immunosuppressive drugs can be classified into four groups: glucocorticoids, cytostatics, antibodies, drugs acting on immunophilins, and other drugs such as interferons, opiates INF binding proteins, mycophenolate, FTY720 and the like. A particular class of immunosuppressant drugs comprises those drugs that act on immunophilins. Immunophilins are an example of high-affinity, specific binding proteins having physiological significance. Two distinct families of immunophilins are presently known: cyclophilins and macrophilins, the latter of which specifically bind, for example, tacrolimus or sirolimus. The immunosuppressant drugs that act on immunophilin include, for example, cyclosporin (including cyclosporin A, cyclosporin B, cyclosporin C, cyclosporin D, cyclosporin E, cyclosporin F, cyclosporin G, cyclosporin H, cyclosporin I), tacrolimus (FK506, PROGRAF®), sirolimus (rapamycin, RAPAMUNE®), and everolimus (RAD, CERTICAN®), for example.

As mentioned above, some examples in accordance with the principles described herein are directed to methods of determining a true total amount of an analyte in an unknown sample suspected of containing the analyte in the presence of endogenous interfering substances. The assay and assay reagents are first used on known samples that are substantially free from endogenous interfering substances to determine certain coefficients. An equation employing these coefficients then may be used to calculate total analyte amounts in unknown samples, in the presence of endogenous interfering substances, simply by determining an amount of analyte in the unknown sample that is bound by endogenous binding substances and using the equation. As discussed above, assays are conducted on samples containing known amounts of the analyte to determine amounts of free analyte and amounts of bound analyte for each of the samples containing differing but known amounts of analyte. From a regression analysis of the plot of data from measurements of free analyte and bound analyte, coefficients are determined that may be used in an equation to calculate total analyte concentration in samples containing unknown amounts of the analyte regardless of the presence of endogenous interfering substances.

As mentioned above, the coefficients are determined by conducting assays on samples containing known amounts of analyte and plotting the resulting data. The samples are substantially free from endogenous interfering substances. The concentration of analyte in the known samples should span the suspected concentration range of interest of the analyte in the unknown samples. The known samples may be prepared by adding known amounts of analyte to a biological sample or a non-biological sample similar to the preparation of calibrators. On the other hand, the samples can be selected from those that are known to contain certain amounts of analyte but are substantially free from endogenous interfering substances. In either approach the number of samples of differing known analyte concentrations for determining the coefficients is dependent on one or more of the nature of the analyte, the nature of the sample, the nature of endogenous binding substances, and the nature of the assay reagents or components, for example. In examples in accordance with the principles described herein the number of samples of differing known analyte concentrations for the determination should be about 2 to about 10, or about 3 to about 10, or about 4 to about 10, or about 4 to about 8, or about 4 to about 6, or about 4 to about 5, or about 5 to about 7, for example. The known amounts of analyte should vary from one sample to another by about 1% to about 10,000%, or about 10% to about 1,000%, or about 50% to about 300%, for example, with a difference between 0 amount of analyte and the next highest amount being at least about 30 ng/mL, or at least about 50 ng/mL, or at least about 75 ng/mL, for example. In some examples, the samples containing known amounts of analyte are prepared by spiking a sample with a desired amount of the analyte.

As mentioned above, the known samples should be substantially free from interfering substances. The phrase "substantially free from interfering substances" means that the known samples do not contain such substances in an amount that affects the measurement result by more than about 10%, or by more than about 5%, or by more than about 3%, or by more than 1%. In some examples in accordance with the principles described herein, samples substantially free from interfering substances may be obtained by subjecting samples to analysis by a method such as, but not limited to, liquid chromatography, mass spectrometry, or a combination of thereof such as, for example, liquid chromatography-tandem mass spectrometry, high performance liquid chromatography (HPLC)-tandem mass spectrometry ($LCMS^2$), for example, and choosing samples that are negative for interfering substances. Other approaches include conducting the assay in question on the samples and selecting those that give substantially no signal related to the analyte. The phrase "substantially no signal related to the analyte" means that signal measured in the assay is not detectable or the ratio of bound analyte over total analyte ($[Y]/[X]$) is greater than about 50%, or greater than about 60%, or greater than about 70%, or greater than about 80%, or about greater than 90%, or greater than about 95%, or greater than about 99%, or is the range of about 50% to about 99.99% or about 60% to about 99.99% or about 70% to about 99.99% or about 80% to about 99.99% or about 90% to about 99.99%.

The assay on the known samples is that assay that is to be used on the unknown samples. The determination of the coefficients is for the assay method and assay reagents that are used to conduct the assay on unknown samples. The assay is conducted on the samples containing known amounts of analyte both in the presence of a displacing agent (to measure an amount of bound analyte and an amount of free analyte) and in the absence of a displacing agent (to measure the amount of free analyte). Assay signal that is measured on the various samples is converted into values for the amount of free analyte in the sample plus analyte that is bound by endogenous binding substances (assay carried out with addition of a displacing agent) and into values for the amount of only free analyte in the sample (assay carried out in the absence of a displacing agent). Subtraction of the latter from the former yields the amount of analyte in the sample that is bound by endogenous binding substances. The results are subjected to regression analysis where the amount of free analyte in the sample is plotted against the amount of bound analyte in the sample. One coefficient is variable and corresponds to the slope of the regression and one coefficient is constant and corresponds to the intercept of the regression. The values of the variable (dependent) coefficient and the constant (independent) coefficient may then be used to calculate a total amount of the analyte in samples that contain unknown amounts of analyte and potentially contain endogenous interfering substances, as explained more fully below.

The methods for determining total analyte amounts in unknown samples involve measuring an amount [Y] of the analyte in the unknown sample that represents analyte that is bound by endogenous binding substances (bound analyte) employing an assay for the analyte. An amount [Z] of analyte in the unknown sample that is not bound by endogenous binding substances (free analyte) is determined by the formula: $[Z]=a[Y]+b$, wherein "a" and "b" are coefficients referred to above for assays conducted on samples containing known amounts of the analyte but substantially free from interfering substances. Adding [Y] and [Z] yields the total amount [X] of the analyte in the unknown sample, which is determined in the presence of endogenous interfering substances in the unknown sample. Coefficient "a" is a dependent coefficient and coefficient "b" is an independent coefficient. As mentioned above, coefficients "a" and "b" are determined by conducting assays on samples containing known amounts of analyte and plotting the resulting data. The values of "a" and "b" may then be used to calculate the total amount of the analyte in samples that contain unknown amounts of analyte in the presence of interfering substances.

Certain aspects of the following discussion apply to assays for both the known samples and the unknown samples. As discussed more fully below, any assay may be employed. The assay comprises adding reagents for determining the concentration of the analyte in the sample to a medium comprising the sample. In some embodiments the assay is an immunoassay and the reagents comprise at least one antibody for the analyte. An amount of a complex comprising the antibody for the analyte is measured. Measurement of a level of signal generated by free analyte only and that generated by free analyte plus analyte that is bound by endogenous binding substances are conducted using the assay. The assays conducted on the sample portions may be carried out sequentially or concomitantly in separate reaction vessels or sequentially in the same reaction vessel for each sample portion. The phrase "complex comprising the antibody for the analyte" refers to a complex wherein the antibody for the analyte is complexed to analyte in the sample.

The amount of the bound analyte is measured by subjecting a portion of a sample to an assay wherein, prior to or during the assay, the sample is treated with an agent that displaces the bound analyte from endogenous binding substances. The displacing agent displaces analyte that is bound by endogenous binding substances. In this manner the amount of analyte that is measured is that which was bound by the endogenous binding substances but is now displaced plus the amount of free analyte (that is analyte in the sample that is not bound by endogenous binding substances). To measure an amount of free analyte, another portion of the sample is subjected to an assay wherein the sample is not treated with such a displacing agent. Subtraction of the latter from the former yields an amount [Y] of analyte that is bound by endogenous binding substances in the sample. An agent that displaces analyte from endogenous binding substances is referred to herein as a displacing agent. The nature of the displacing agent is dependent on one or more of the nature of the analyte and, to a lesser degree, the nature of the endogenous binding substances, for example.

As mentioned above, measurements of analyte are carried out on samples that have been treated with a displacing agent and samples that have not been treated with a displacing agent to determine the amount of bound analyte plus free analyte and the amount of free analyte only, respectively. Subtraction of the latter from the former yields the amount of bound analyte in the sample. As referred to above, a portion of the sample is employed for conducting assays to determine an amount of bound analyte. For the measurements, the sample portion can be prepared in any convenient medium that does not interfere with an assay; an aqueous medium generally is employed. The size of the sample portion is dependent on one or more of the nature of the analyte, the nature of the assay, the nature of the various reagents for conducting the assay, and the nature of the complex comprising the analyte, for example. The size of the sample portion should be substantially the same for both measurements. In some embodiments the volume of the sample portion is about 1 μL to about 100 μL, or about 2 μL to about 100 μL, or about 5 μL to about 100 μL, or about 10

μL to about 100 μL, or about 1 μL to about 80 μL, or about 1 μL to about 60 μL, or about 1 μL to about 40 μL, or about 1 μL to about 20 μL, or about 5 μL to about 50 μL, or about 10 μL to about 50 μL, for example.

The portion of the sample for conducting an assay to obtain a measurement of the analyte that is bound by endogeneous binding substances involves treating the sample with a displacing agent as discussed above. The amount of displacing agent that is added to the sample is that which is sufficient to displace substantially all of the analyte from the endogeneous binding substances so that the signal obtained in an assay on the sample is representative of both the amount of analyte that was bound by the endogeneous binding substances and of the amount of free analyte in the sample. In accordance with the principles described herein, the phrase "displace substantially all of the analyte that is bound by endogeneous binding substances" means that the analyte is at least 80%, or at least 90%, or at least 95%, or at least 99%, or at least 99.5%, or at least 99.9% or is 100% displaced from endogeneous binding substances and available for detection during an assay.

After addition of a displacing agent, the sample is incubated for a period of time under conditions to displace substantially all of the analyte from endogeneous binding substances. The length and conditions of the incubation are dependent on one or more of the nature of the displacing agent, the nature of the analyte, and the suspected concentration of the analyte, for example. In some embodiments incubation temperatures for this step may be about 5° C. to about 99° C., or about 15° C. to about 70° C., or about 20° C. to about 45° C., for example. The time period for the incubation is about 0.2 seconds to about 24 hours, or about 1 second to about 6 hours, or about 2 seconds to about 1 hour, or about 1 to about 15 minutes, for example. The incubation may be carried out in a medium that, for convenience, may be an assay medium as discussed herein, but need not be.

To determine an amount of analyte in the sample that is free, a portion of the same sample is subjected to the assay without treatment with a displacing agent. The assay is carried out as described above for the sample that was treated with a displacing agent. The amount of free analyte is subtracted from the amount of both free analyte and bound analyte as discussed above to obtain an amount of only the bound analyte. For unknown samples, this amount of the bound analyte is employed to calculate the total amount of analyte in the sample. The amount of bound analyte is represented in the above formula by [Y]. Having previously determined values for "a" and "b" for a particular assay and set of assay reagents using samples containing known amounts of analyte but substantially free from endogeneous interfering substances, an amount [Z] of analyte in the unknown sample that is not bound by endogeneous binding substances (free analyte) is determined by the formula: [Z]=a[Y]+b. Adding [Y] and [Z] yields the total amount [X] of the analyte in the unknown sample, which is determined in the presence of interfering substances in the unknown sample.

The displacing agent may be any moiety, either a single compound or a mixture of compounds, which accomplishes the desired result of displacement of analyte from endogeneous binding substances with no significant binding to assay reagents such as, for example, an assay antibody. In some examples the displacing agent displaces the analyte, and its metabolites if required, from endogenous binding substances to render both the analyte and the metabolites substantially accessible to a binding partner for the analyte such as, for example, an antibody for the analyte.

In some embodiments the displacing agent is an analog, including structural analogs, of the analyte. An analyte analog is a modified analyte that can displace the analogous analyte from a binding substance but does not compete to any substantial degree for a receptor such as an antibody for the analyte. The modification may provide means to join an analyte analog to another molecule. The analyte analog will usually differ from the analyte by more than replacement of a hydrogen with a bond which links the analyte analog to a hub or label, but need not. The analyte analog may be, for example, a molecule structurally related to the analyte, and the analyte conjugated to another molecule through a linking group, for example. For analytes that comprise a hydroxyl or carboxylic acid functionality, the displacing agent may be an ester of the analyte, which has a high binding affinity for endogenous binding substances relative to the analyte to be detected and which has no significant binding affinity for an antibody for the analyte. A structural analog is a moiety that has the same or similar structural or spatial characteristics as the analyte such that the structural analog accomplishes the same or similar result as the analog of the analyte in displacing analyte from endogeneous binding substances. The structural analog may be, for example, another compound that is related to the analyte.

In the case of an immunosuppressant drug, the structural analog may be, for example, another compound that is related to the immunosuppressant drug. In an example of a displacing agent for a determination for tacrolimus, by way of illustration and not limitation, an ester of tacrolimus (e.g., FK506) may be employed as the displacing agent so long as it meets the above requirements. In another example, in a determination for sirolimus, an ester of tacrolimus may be employed as the displacing agent. The ester may be, for example, a carbamate, a carbonate, or an ester of a C1 to C6 carboxylic acid. See, for example, U.S. Pat. No. 7,186,518, the relevant disclosure of which is incorporated herein by reference. Other examples of displacing agents include, but are not limited to, [Thr2, Leu5, D-Hiv8, Leu10]-cyclosporin A for cyclosporin A, FK506 for sirolimus, and sirolimus for FK506, for example. See, for example, U.S. Pat. No. 6,187,547, the relevant disclosure of which is incorporated herein by reference.

The concentration of the displacing agent in the medium is that sufficient to achieve the desired result of displacing substantially all of the analyte, and in some instances metabolites of the analyte, from endogeneous binding substances to render the analyte, and metabolites if desired, accessible for binding to an antibody for the analyte as discussed above. The amount or concentration of the displacing agent employed depends on one or more of the nature of the sample, the nature of the analyte, the nature of analyte metabolites, the nature of other reagent components, and the reaction conditions, for example. In some embodiments the amount of the displacing agent is about 0.000001% to about 0.5%, about 0.0001% to about 0.4%, about 0.001% to about 0.3%, about 0.01% to about 0.2%, about 0.1% to about 0.3%, about 0.2% to about 0.5%, about 0.1% to about 0.2%, and so forth (percent is weight/volume).

After addition of a displacing agent, the second sample portion is incubated for a period of time under conditions to substantially release the analyte. The length and conditions of the incubation are dependent on one or more of the nature of the displacing agent, the nature of the analyte, the suspected concentration of the analyte, the antibody affinity and avidity and antibody fragmentation, for example. In some embodiments incubation temperatures for this step may be about 5° C. to about 99° C., or about 15° C. to about 70° C., or about 20° C. to about 45° C., for example. The time period for the incubation is about 0.2 seconds to about 24 hours, or about 1 second to about 6 hours, or about 2 seconds to about 1 hour, or about 1 to about 15 minutes, for example. The incubation is usually carried out in a medium, which for convenience may be an assay medium as discussed herein, but need not be.

In some embodiments a hemolytic agent is employed, which is an agent that disrupts cellular membranes in which the analyte may be entrapped. For example, an analyte that is entrapped within red blood cells may be released from the red blood cells by employing a hemolytic agent. A hemolytic agent is a compound or mixture of compounds that disrupt the integrity of the membranes of red blood cells thereby displacing intracellular contents of the cells and, in particular, erythrocytes. Numerous hemolytic agents are known in the art. Hemolytic agents include, for example, non-ionic detergents, anionic detergents, amphoteric detergents, low ionic strength aqueous solutions (hypotonic solutions), bacterial agents, antibodies that cause complement dependent lysis, and the like.

Non-ionic detergents that may be employed as the hemolytic agent include both synthetic detergents and natural detergents. Examples of synthetic detergents include TRITON™ X-100, TRITON™ N-101, TRITON™ X-114, TRITON™ X-405, TRITON™ SP-135, TWEEN® 20 (polyoxyethylene (20) sorbitan monolaurate), TWEEN® 80 (polyoxyethylene (20) sorbitan monooleate), DOWFAX®, ZONYL®, pentaerythrityl palmitate, ADOGEN® 464, ALKANOL® 6112 surfactant, allyl alcohol 1,2-butoxylate-block-ethoxylate HLB 6, BRIJ®, ethylenediamine tetrakis (ethoxylate-block-propoxylate) tetrol, IGEPAL®, MERPOL®, poly(ethylene glycol), 2-[ethyl[(heptadecafluorooctyl)sulfonyl]amino]ethyl ether, polyethylene-block-poly(ethylene glycol), polyoxyethylene sorbitan tetraoleate, polyoxyethylene sorbitol hexaoleate, TERGITOL® NP-9, GAFAC® (RHODAFAC®, an alkyl polyoxyethylene glycol phosphate ester such as, for example, alpha-dodecyl-omega-hydroxypoly(oxy-1,2-ethanediyl) phosphate), and EP110® and the like. Naturally-occurring detergents that may be employed as the hemolytic agent include, for example, saponins, sodium or potassium neutralized fatty acid, neutralized phospholipids, diacylglycerol, neutralized phosphatidyl serine, phosphatidate, neutralized phosphatidyl ethanolamine, phosphatidyl choline, phosphatidyl inositol, phosphatidylcholine, bile salt, unesterified cholesterol, neutralized sphingosine, ceramide, and the like. Combinations of one or more synthetic detergents or one or more naturally occurring detergents and combinations of synthetic detergents and naturally occurring detergents may also be employed.

Other agents that may be employed in the present embodiments include solubility reagents such as, for example, a small amount of an organic solvent such as, e.g., methanol, ethanol, isopropanol, methoxy propanol and dimethylsulfoxide (DMSO); and agents for carrying out protein digestion such as, for example, proteinases, trypsin, pepsin, and peptidases; for example.

General Description of Assays for an Analyte

Any suitable assay may be employed for determining assay measurement results, as discussed above. The assays may be conducted on the sample portions as an immediate continuation of the treatment of the portions with a displacing agent as discussed above or the assay may be carried out at a point thereafter. The assays are conducted by combining the respective sample portions with reagents for determining the amount of the analyte in the sample. The nature of the reagents is dependent on the particular type of assay to be performed. In general, the assay is a method for the determination of the amount of an analyte in a sample. The assay may be an immunoassay or a non-immunoassay. Various assay methods are discussed below by way of illustration and not limitation.

In many embodiments the reagents comprise at least one antibody for the analyte and the assay is generally referred to as an immunoassay as distinguished from assays that do not utilize an antibody, which are referred to as non-immunoassays. By the phrase "antibody for the analyte" is meant an antibody that binds specifically to the analyte (and to metabolites of the analyte if desired) and does not bind to any significant degree to other substances that would distort the analysis for the analyte.

One general group of immunoassays that may be employed includes immunoassays using a limited concentration of antibody. Another group of immunoassays involves the use of an excess of one or more of the principal reagents such as, for example, an excess of an antibody for the analyte. Another group of immunoassays are separation-free homogeneous assays in which the labeled reagents modulate the label signal upon analyte-antibody binding reactions. Another group of assays includes labeled antibody reagent limited competitive assays for analyte that avoid the use of problematic labeled haptens. In this type of assay, a solid phase immobilized analyte is present in a constant, limited amount. The partition of a label between the immobilized analyte and non-immobilized analyte depends on the concentration of analyte in the sample.

Antibodies specific for an analyte for use in immunoassays can be monoclonal or polyclonal. Such antibodies can be prepared by techniques that are well known in the art such as immunization of a host and collection of sera (polyclonal) or by preparing continuous hybrid cell lines and collecting the secreted protein (monoclonal) or by cloning and expressing nucleotide sequences or mutagenized versions thereof coding at least for the amino acid sequences required for specific binding of natural antibodies.

Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')$_2$, and Fab', for example. In addition, aggregates, polymers, and conjugates of immunoglobulins or their fragments can be used where appropriate so long as binding affinity for a particular molecule is maintained.

As discussed above, an antibody selected for use in an immunoassay for an analyte, for example, should specifically and preferentially bind the analyte (and its pharmaceutically active metabolites, if necessary or desired) over other ligands such as other metabolites or related substances.

Other reagents are included in the assay medium depending on the nature of the assay to be conducted. Such assays usually involve reactions between binding partners such as an analyte and a corresponding antibody or the binding between an antibody and a corresponding binding partner such as a second antibody that binds to the first antibody. Accordingly, the binding partner may be a protein, which may be an antibody or an antigen. The binding partner may be a member of a specific binding pair ("sbp member"), which is one of two different molecules, having an area on the surface or in a cavity, which specifically binds to and is thereby defined as complementary with a particular spatial and polar organization of the other molecule. The members of the specific binding pair will usually be members of an immunological pair such as antigen-antibody, although other specific binding pairs such as, for example, biotin-avidin, hormones-hormone receptors, enzyme-substrate, nucleic acid duplexes, IgG-protein A, and polynucleotide pairs such as DNA-DNA, DNA-RNA, are not immunological pairs but are included within the scope of the term "sbp member."

As discussed above, specific binding involves the specific recognition of one of two different molecules for the other compared to substantially less recognition of other molecules. On the other hand, non-specific binding involves non-covalent binding between molecules that is relatively independent of specific surface structures. Non-specific binding may result from several factors including hydrophobic interactions between molecules. In many embodiments of assays, preferred binding partners are antibodies and the assays are referred to as immunoassays.

The immunoassays may involve labeled or non-labeled reagents. Immunoassays involving non-labeled reagents usually comprise the formation of relatively large complexes involving one or more antibodies. Such assays include, for example, immunoprecipitin and agglutination methods and corresponding light scattering techniques such as, e.g., nephelometry and turbidimetry, for the detection of antibody complexes. Labeled immunoassays include enzyme immunoassays, fluorescence polarization immunoassays, radioimmunoassay, inhibition assay, induced luminescence, and fluorescent oxygen channeling assay, for example.

In some embodiments homogeneous immunoassays may be employed; such assays may also be referred to as essentially partition-free immunoassays. The present methods have application to fully automated homogeneous assays in which, prior to the assay, there is no extraction or separation of the analyte from other constituents of the sample including analyte metabolites. In a "non-manual extraction" assay, a sample such as a whole blood sample, without extraction in, e.g., an organic solvent, is combined with reagents for conducting an assay for the analyte in a suitable medium and the assay method is conducted. The present methods also find application to manual extraction assays.

The assays can be performed either without separation (homogeneous) or with separation (heterogeneous) of any of the assay components or products. Homogeneous immunoassays are exemplified by the EMIT® assay (Syva Company, San Jose, Calif.) disclosed in Rubenstein, et al., U.S. Pat. No. 3,817,837, column 3, line 6 to column 6, line 64; immunofluorescence methods such as those disclosed in Ullman, et al., U.S. Pat. No. 3,996,345, column 17, line 59, to column 23, line 25; enzyme channeling immunoassays ("ECIA") such as those disclosed in Maggio, et al., U.S. Pat. No. 4,233,402, column 6, line 25 to column 9, line 63; the fluorescence polarization immunoassay ("FPIA") as disclosed, for example, in, among others, U.S. Pat. No. 5,354,693; and so forth.

Other enzyme immunoassays are the enzyme modulate mediated immunoassay ("EMMIA") discussed by Ngo and Lenhoff, FEBS Lett. (1980) 116:285-288; the substrate labeled fluorescence immunoassay ("SLFIA") disclosed by Oellerich, J. Clin. Chem. Clin. Biochem. (1984) 22:895-904; the combined enzyme donor immunoassays ("CEDIA") disclosed by Khanna, et al., Clin. Chem. Acta (1989) 185:231-240; homogeneous particle labeled immunoassays such as particle enhanced turbidimetric inhibition immunoassays ("PETINIA"), particle enhanced turbidimetric immunoassay ("PETIA"), etc.; and the like.

Other assays include the sol particle immunoassay ("SPIA"), the disperse dye immunoassay ("DIA"); the metalloimmunoassay ("MIA"); the enzyme membrane immunoassays ("EMIA"); luminoimmunoassays ("LIA"); acridinium ester label immunoassays using paramagnetic particles as a solid phase (ADVIA Centaur immunoassays); and so forth. Other types of assays include immunosensor assays involving the monitoring of the changes in the optical, acoustic and electrical properties of an antibody-immobilized surface upon the binding of a hydrophobic drug. Such assays include, for example, optical immunosensor assays, acoustic immunosensor assays, semiconductor immunosensor assays, electrochemical transducer immunosensor assays, potentiometric immunosensor assays, amperometric electrode assays, and the like.

In many of the assays discussed herein for determination of an analyte, a label is employed; the label is usually part of a signal producing system ("sps"). The nature of the label is dependent on the particular assay format. An sps usually includes one or more components, at least one component being a detectable label, which generates a detectable signal that relates to the amount of bound and/or unbound label, i.e. the amount of label bound or not bound to the analyte being detected or to an agent that reflects the amount of the analyte to be detected. The label is any molecule that produces or can be induced to produce a signal, and may be, for example, a fluorescer, a radiolabel, an enzyme, a chemiluminescer or a photosensitizer. Thus, the signal is detected and/or measured by detecting enzyme activity, luminescence, light absorbance or radioactivity, depending on the nature of the label.

Suitable labels include, by way of illustration and not limitation, enzymes such as alkaline phosphatase, glucose-6-phosphate dehydrogenase ("G6PDH"), β-galatosidase, and horseradish peroxidase; ribozyme; a substrate for a replicase such as QB replicase; promoters; dyes; fluorescers, such as fluorescein, isothiocyanate, rhodamine compounds, phycoerythrin, phycocyanin, allophycocyanin, o-phthaldehyde, and fluorescamine; complexes such as those prepared from CdSe and ZnS present in semiconductor nanocrystals known as Quantum dots; chemiluminescers such as isoluminol and acridinium esters, for example; sensitizers; coenzymes; enzyme substrates; radiolabels such as $^{125}$I, $^{131}$I, $^{14}$C, $^{3}$H, $^{57}$Co and $^{75}$Se; particles such as latex particles, carbon particles, metal particles including magnetic particles, e.g., chromium dioxide ($CrO_2$) particles, and the like; metal sol; crystallite; liposomes; cells, etc., which may be further labeled with a dye, catalyst or other detectable group. Suitable enzymes and coenzymes are disclosed in Litman, et al., U.S. Pat. No. 4,275,149, columns 19-28, and Boguslaski, et al., U.S. Pat. No. 4,318,980, columns 10-14; suitable fluorescers and chemiluminescers are disclosed in Litman, et al., U.S. Pat. No. 4,275,149, at columns 30 and 31; which are incorporated herein by reference.

The label can directly produce a signal and, therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. Other labels that directly produce a signal include radioactive isotopes and dyes.

Alternately, the label may need other components to produce a signal, and the signal producing system would then include all the components required to produce a measurable signal. Such other components may include substrates, coenzymes, enhancers, additional enzymes, substances that react with enzymic products, catalysts, activators, cofactors, inhibitors, scavengers, metal ions, and a specific binding substance required for binding of signal generating substances. A detailed discussion of suitable signal producing systems can be found in Ullman, et al., U.S. Pat. No. 5,185,243, columns 11-13, incorporated herein by reference.

The label or other sps members can be bound to a support. An analyte or analyte analog may be bound to a solid support in any manner known in the art, provided only that the binding does not substantially interfere with the analyte's or analog's ability to bind with an antibody. In some embodiments, the analyte or analyte analog may be coated or covalently bound directly to the solid phase or may have layers of one or more carrier molecules such as poly(amino acids) including proteins such as serum albumins or immunoglobulins, or polysaccharides (carbohydrates) such as, for example, dextran or dextran derivatives. Linking groups may also be used to covalently couple the solid support and the analyte. Other methods of binding the analyte are also possible. For instance, a solid support may have a coating of a binder for a small molecule such as, for example, avidin, an antibody, etc., and a small molecule such as, e.g., biotin, hapten, etc., can be bound to the analyte or vice versa. The binding of components to the surface of a support may be direct or indirect, covalent or non-covalent and can be accomplished by well-known techniques, commonly available in the literature. See, for example, "Immobilized Enzymes," Ichiro Chibata, Halsted Press, New York (1978) and Cautrecasas, *J. Biol. Chem.*, 245:3059 (1970).

The support may be comprised of an organic or inorganic, solid or fluid, water insoluble material, which may be transparent or partially transparent. The support can have any of a number of shapes, such as particle, including bead, film, membrane, tube, well, strip, rod, planar surfaces (such as, e.g., plate, and paper), and fiber, for example. Depending on the type of assay, the support may or may not be suspendable in the medium in which it is employed. Examples of suspendable supports are polymeric materials such as latex, lipid bilayers or liposomes, oil droplets, cells and hydrogels, and magnetic particles, for example. Other support compositions include polymers, such as nitrocellulose, cellulose acetate, poly (vinyl chloride), polyacrylamide, polyacrylate, polyethylene, polypropylene, poly(4-methylbutene), polystyrene, polymethacrylate, poly (ethylene terephthalate), nylon, and poly(vinyl butyrate), either used by themselves or in conjunction with other materials.

The support may be a particle. The particles should have an average diameter of at least about 0.02 microns and not more than about 100 microns. In some embodiments, the particles have an average diameter from about 0.05 microns to about 20 microns, or from about 0.3 microns to about 10 microns. The particle may be organic or inorganic, swellable or non-swellable, porous or non-porous, preferably of a density approximating water, generally from about 0.7 g/mL to about 1.5 g/mL, and composed of material that can be transparent, partially transparent, or opaque. The particles can be biological materials such as cells and microorganisms, e.g., erythrocytes, leukocytes, lymphocytes, hybridomas, *streptococcus, Staphylococcus aureus, E. coli*, viruses, and the like. The particles can also be particles comprised of organic and inorganic polymers, liposomes, latex particles, magnetic or non-magnetic particles, phospholipid vesicles, chylomicrons, lipoproteins, and the like. In some embodiments, the particles are chromium dioxide (chrome) particles or latex particles.

The polymer particles can be formed of addition or condensation polymers. The particles will be readily dispersible in an aqueous medium and can be adsorptive or functionalizable so as to permit conjugation to an analyte, either directly or indirectly through a linking group. The particles can also be derived from naturally occurring materials, naturally occurring materials that are synthetically modified, and synthetic materials. Among organic polymers of particular interest are polysaccharides, particularly cross-linked polysaccharides, such a agarose, which is available as SEPHAROSE®, dextran, available as SEPHADEX® and SEPHACRYL®, cellulose, starch, and the like; addition polymers, such as polystyrene, polyvinyl alcohol, homopolymers and copolymers of derivatives of acrylate and methacrylate, particularly esters and amides having free hydroxyl functionalities, for example.

The label and/or other sps member may be bound to an sbp member or another molecule. For example, the label can be bound covalently to an sbp member such as, for example, an antibody, a receptor for an antibody, a receptor that is capable of binding to a small molecule conjugated to an antibody, or an analyte analog. Bonding of the label to the sbp member may be accomplished by chemical reactions that result in replacing a hydrogen atom of the label with a bond to the sbp member or may include a linking group between the label and the sbp member. Other sps members may also be bound covalently to sbp members. For example, two sps members such as a fluorescer and quencher can each be bound to a different antibody that forms a specific complex with the analyte. Formation of the complex brings the fluorescer and quencher in close proximity, thus permitting the quencher to interact with the fluorescer to produce a signal. Methods of conjugation are well known in the art. See, for example, Rubenstein, et al., U.S. Pat. No. 3,817, 837, incorporated herein by reference.

Enzymes of particular interest as label proteins are redox enzymes, particularly dehydrogenases such as glucose-6-phosphate dehydrogenase, and lactate dehydrogenase, for example, and enzymes that involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme which employs the hydrogen peroxide to oxidize a dye precursor, that is, a peroxidase such as horse radish peroxidase, lactoperoxidase, or microperoxidase. Additional enzyme combinations are known in the art. When a single enzyme is used as a label, other enzymes may find use such as hydrolases, transferases, and oxidoreductases, preferably hydrolases such as alkaline phosphatase and beta-galactosidase. Alternatively, luciferases may be used such as firefly luciferase and bacterial luciferase.

Illustrative co-enzymes that find use include NAD[H], NADP[H], pyridoxal phosphate, FAD[H], FMN[H], etc., usually coenzymes involving cycling reactions. See, for example, U.S. Pat. No. 4,318,980, the disclosure of which is incorporated herein by reference.

With label proteins such as, for example, enzymes, the molecular weight range will be from about 10,000 to about 600,000, or from about 10,000 to about 300,000 molecular weight. There is usually at least about 1 analyte analog per about 200,000 molecular weight, or at least about 1 per about 150,000 molecular weight, or at least about 1 per about 100,000 molecular weight, or at least about 1 per about 50,000 molecular weight, for example. In the case of enzymes, the number of analyte analog groups is from 1 to about 20, about 2 to about 15, about 3 to about 12, or about 6 to about 10, for example.

The term "non-poly(amino acid) labels" includes those labels that are not proteins (e.g., enzymes). The non-poly (amino acid) label is capable of being detected directly or is detectable through a specific binding reaction that produces a detectable signal. The non-poly(amino acid) labels include, for example, radioisotopes, luminescent compounds, supports, e.g., particles, plates, beads, etc., polynucleotides, and the like. More particularly, the non-poly (amino acid) label can be isotopic or non-isotopic, usually non-isotopic, and can be a polynucleotide coding for a catalyst, promoter, dye, coenzyme, enzyme substrate, radioactive group, a small organic molecule (including, e.g., biotin, fluorescent molecules, chemiluminescent molecules, and the like), amplifiable polynucleotide sequence, a support such as, for example, a particle such as latex or carbon particle or chromium dioxide (chrome) particle, a metal sol, a crystallite, a liposome, or a cell, which may or may not be further labeled with a dye, catalyst or other detectable group, for example.

In one embodiment the assay is an induced luminescence immunoassay, which is described in U.S. Pat. No. 5,340,716 (Ullman, et al.) entitled "Assay Method Utilizing Photoactivated Chemiluminescent Label" ("induced luminescence assay"), which disclosure is incorporated herein by reference. In one approach the assay uses a particle incorporating a photosensitizer and a label particle incorporating a chemiluminescent compound. The label particle is conjugated to an sbp member, for example, an antibody for the analyte that is capable of binding to the analyte to form a complex, or to a second sbp member to form a complex, in relation to the amount of the analyte. If the analyte is present, the photosensitizer and the chemiluminescent compound come into close proximity. The photosensitizer generates singlet oxygen and activates the chemiluminescent compound when the two labels are in close proximity. The activated chemiluminescent compound subsequently produces light. The amount of light produced is related to the amount of the complex formed, which comprises antibody for the analyte.

By way of further illustration, chemiluminescent particles are employed, which comprise the chemiluminescent compound associated therewith such as by incorporation therein or attachment thereto. An sbp member that binds to the analyte, such as, for example, an antibody for analyte, is bound to a polysaccharide coating the particles. A second sbp member that binds to the analyte is part of a biotin conjugate. Streptavidin is conjugated to a second set of particles having a photosensitizer associated therewith. The binding of the streptavidin to this second set of particles (photosensitizer particles) may or may not involve a polysaccharide on the particles. The chemiluminescent particles are mixed with the respective portion of the sample suspected of containing an analyte and with the photosensitizer particles. With regard to the first portion of the sample, the reaction medium is incubated to allow the particles to bind to substances or components in the sample other than analyte. With regard to the second portion of the sample, the reaction medium is incubated to allow the particles to bind to the analyte by virtue of the binding of the sbp members to the analyte. Then, the medium is irradiated with light to excite the photosensitizer, which is capable in its excited state of activating oxygen to a singlet state. Because the chemiluminescent compound of one of the sets of particles is now in close proximity to the photosensitizer by virtue of the presence of the analyte, it is activated by singlet oxygen and emits luminescence. The medium is then examined for the amount of luminescence or light emitted, the presence thereof being related to the amount of the analyte.

Another particular example of an assay that may be employed for the determination of an analyte is discussed in U.S. Pat. No. 5,616,719 (Davalian, et al.), which describes fluorescent oxygen channeling immunoassays.

The assays discussed above are normally carried out in an aqueous buffered medium at a moderate pH, generally that which provides optimum assay sensitivity. The pH for the assay medium will usually be in the range of about 4 to about 11, or in the range of about 5 to about 10, or in the range of about 6.5 to about 9.5. The pH will usually be a compromise between optimum binding of the binding members of any specific binding pairs, and the pH optimum for other reagents of the assay such as members of a signal producing system, for example. Various buffers may be used to achieve the desired pH and maintain the pH during the incubation period. Illustrative buffers include borate, phosphate, carbonate, Tris, barbital, PIPES, HEPES, MES, ACES, MOPS, BICINE, and the like. The medium may also comprise agents for preventing the formation of blood clots. Such agents are well known in the art and include, for example, ethylenediamine tetraacetate (EDTA), ethylene glycol tetraacetate (EGTA), citrate, heparin, and the like. Various ancillary materials may be employed in the assay methods. For example, in addition to buffers and preservatives, the medium may comprise stabilizers for the medium and for the reagents employed. In some embodiments, in addition to these additives, proteins may be included, such as albumins; quaternary ammonium salts; polyanions such as dextran sulfate; and binding enhancers, for example. All of the above materials are present in a concentration or amount sufficient to achieve the desired effect or function.

One or more incubation periods may be applied to the medium at one or more intervals including any intervals between additions of various reagents mentioned above. The medium is usually incubated at a temperature and for a time sufficient for binding of various components of the reagents to occur. Moderate temperatures are normally employed for carrying out the method and usually constant temperature, preferably, room temperature, during the period of the measurement. Incubation temperatures normally range from about 5° C. to about 99° C., or from about 15° C. to about 70° C., or about 20° C. to about 45° C., for example. The time period for the incubation is about 0.2 seconds to about 24 hours, or about 1 second to about 6 hours, or about 2 seconds to about 1 hour, or about 1 to about 15 minutes, for example. The time period depends on the temperature of the medium and the rate of binding of the various reagents. Temperatures during measurements will generally range from about 10° C. to about 50° C., or from about 15° C. to about 40° C.

The concentration of analyte that may be assayed generally varies from about $10^{-5}$ to about $10^{-17}$ M, or from about $10^{-6}$ to about $10^{-14}$ M. Considerations, such as whether the assay is qualitative, semi-quantitative or quantitative (relative to the amount of erythrocytophilic drug analyte present in the sample), the particular detection technique and the concentration of the analyte normally determine the concentrations of the various reagents.

The concentrations of the various reagents in the assay medium will generally be determined by the concentration range of interest of the analyte, the nature of the assay, the antibody affinity and avidity and antibody fragmentation, for example. However, the final concentration of each of the reagents is normally determined empirically to optimize the sensitivity of the assay over the range. That is, a variation in concentration of analyte that is of significance should provide an accurately measurable signal difference. Considerations such as the nature of a signal producing system and the nature of the analyte normally determine the concentrations of the various reagents.

While the order of addition may be varied widely, there will be certain preferences depending on the nature of the assay. The simplest order of addition is to add all the materials simultaneously and determine the effect that the assay medium has on the signal as in a homogeneous assay. Alternatively, the reagents can be combined sequentially. Optionally, an incubation step may be involved subsequent to each addition as discussed above. The length of the incubation period is that which is sufficient to accomplish the desired function.

Specific Embodiments of Assays for Certain Immunosuppressant Analytes

Specific embodiments of assays that may be employed to assay the respective sample portions are discussed next by way of illustration and not limitation for immunosuppressant analytes.

In a homogeneous assay, after all of the reagents have been combined, the signal is determined and related to the amount of analyte in the sample. For example, in an EMIT® assay for an analyte, a sample suspected of containing the analyte is combined in an aqueous medium either simultaneously or sequentially with an enzyme conjugate of the analyte, i.e., an analog of the analyte, and antibody capable of recognizing the analyte. Generally, a substrate for the enzyme is added, which results in the formation of a chromogenic or fluorogenic product upon enzyme catalyzed reaction. Preferred enzymes are glucose-6-phosphate dehydrogenase and alkaline phosphatase but other enzymes may be employed. The analyte and the moieties of the enzyme conjugate compete for binding sites on the antibody. The enzyme activity in the medium is then measured, usually by spectrophotometric means.

The aforementioned assays may be carried out using mutant glucose-6-phosphate dehydrogenase as the enzyme of the enzyme conjugate. This mutant enzyme is described in U.S. Pat. Nos. 6,090,567 and 6,033,890, the relevant disclosures of which are incorporated herein by reference. Furthermore, the assay may be conducted using antibodies for the analyte and using procedures as disclosed in U.S. Pat. Nos. 5,328,828 and 5,135,863, the relevant disclosures of which are incorporated herein by reference.

Heterogeneous assays usually involve one or more separation steps and can be competitive or non-competitive. A variety of competitive and non-competitive assay formats are disclosed in Davalian, et al., U.S. Pat. No. 5,089,390, column 14, line 25 to column 15, line 9, which disclosure is incorporated herein by reference. In one type of competitive assay, a support, as discussed herein, having antibodies for the analyte bound thereto is contacted with a medium containing the sample and appropriate enzyme conjugates of the analyte. After separating the support and the medium, the enzyme activity of the support or the medium is determined by conventional techniques to determine the measurement result.

In certain embodiments a second enzyme may be employed in addition to the enzyme of the enzyme conjugate. The enzymes of the pair of enzymes are related in that a product of the first enzyme serves as a substrate for the second enzyme.

Another embodiment of an assay format is a capture assay. In this assay format, the antibody for the analyte is covalently bound to a magnetic particle. The sample is incubated with these particles to allow the antibodies for the analyte to bind to the analyte. Subsequently, an enzyme that has the analyte or a derivative of the analyte covalently attached is incubated with the magnetic particles. After washing, the amount of enzyme that is bound to the magnetic particles is measured and is inversely related to the amount of a complex comprising the antibody for the analyte.

The following assay descriptions are by way of illustration of, and not as a limitation on, the scope of the present examples. Selection of tacrolimus or sirolimus as the immunosuppressant drug is also by way of illustration and not limitation as the present invention has general application to detection of immunosuppressant drugs in particular and other analytes in general.

In one embodiment, the sample portion is mixed with a tacrolimus conjugate, i.e., for example, an analog of tacrolimus that is attached to biotin. Depending on the portion of the sample being analyzed, the sample portion is incubated to allow binding of substances in the sample other than analyte to bind to an antibody for tacrolimus or to allow binding of such substances and the tacrolimus of the sample to bind to the antibody for tacrolimus in competition with the analog of tacrolimus where the antibody is capable of binding to tacrolimus or the analog of tacrolimus. After rinsing with an appropriate wash buffer, a detection molecule consisting of streptavidin or avidin conjugated to an enzyme, florescent or chemiluminescent molecule or radioactive moiety can be added to the medium, which is then examined for the amount of signal. The amount of signal is related to the amount of tacrolimus in the sample.

In one embodiment the assay employed is an induced luminescence assay as described above. In some embodiments of the induced luminescence assay by way of illustration and not limitation, the reagents include two latex bead reagents and a biotinylated anti-tacrolimus mouse monoclonal antibody. The first bead reagent is coated with tacrolimus or a tacrolimus analog and contains chemiluminescent dye. The second bead reagent is coated with streptavidin and contains a photosensitizer dye. Portions of a sample suspected of containing tacrolimus are treated as described above. One sample portion is treated with an antibody for tacrolimus without treatment with a displacing agent. The sample portion is incubated with biotinylated antibody for tacrolimus, which allows tacrolimus in the sample to bind to biotinylated antibody. In a second step, the first bead reagent is added and leads to the formation of bead/biotinylated antibody immunocomplexes with the fraction of the biotinylated antibody that does not bind to analyte. The second bead reagent is then added and binds to the biotin to form bead pair immunocomplexes. When illuminated by light at 680 nm, the second bead reagent converts dissolved oxygen in the reaction solution into the more energetic singlet oxygen form. In the bead pairs, the singlet oxygen diffuses into the first bead reagent thereby triggering a chemiluminescent reaction. The resulting chemiluminescent signal is measured at 612 nm and is an inverse function of the concentration of the substances other that tacrolimus in the sample that bind to tacrolimus antibody. The amount of this signal is related to the amount of such substances in the sample.

The same assay is also carried out on another sample portion, which is treated with FK506 to release tacrolimus from endogenous binding substances in the sample. After conducting the assay, the resulting chemiluminescent signal is measured at 612 nm and is an inverse function of the concentration of tacrolimus in the sample (both free tacrolimus and tacrolimus that was bound to endogeneous binding substances) that binds to tacrolimus antibody. Subtraction of the amount of free tacrolimus from the amount of free tacrolimus plus that which was displaced gives the amount of bound tacrolimus in the sample and the values may be used in the aforementioned equation to calculate total amount of tacrolimus in the sample in the presence of endogeneous interfering substances.

An example, by way of illustration and not limitation, of another assay format is ACMIA (Affinity Chromium dioxide Mediated Immuno Assay). For the ACMIA assay format, chrome particles, which are coated with sirolimus or a sirolimus analog, are employed as a first component. A second component is an antibody for sirolimus. This antibody, crosslinked to a reporter enzyme (for example, β-galactosidase), is added to a reaction vessel in an excess amount, i.e., an amount greater than that required to bind all of the sirolimus analyte that might be present in a sample. A sample suspected of containing sirolimus is divided into equal portions. One sample portion, which was not subjected to treatment with a displacing agent, is treated with an antibody for sirolimus, which binds to free sirolimus but not to other reagents employed in the assay or to interfering substances in the sample. The antibody-enzyme conjugate is mixed with sample portion to allow the sirolimus analyte to bind to the antibody. Next, the chrome particle reagent is added to bind up any excess antibody-enzyme conjugate. Then, a magnet is applied, which pulls all of the chrome particles and excess antibody-enzyme out of the suspension, and the supernatant is transferred to a final reaction container. The substrate of the reporter enzyme is added to the final reaction container, and the enzyme activity is measured spectrophotometrically as a change in absorbance over time. The amount of this signal is related to the amount of free sirolimus in the sample.

The same assay is also carried out on another sample portion, which is treated with a tacrolimus ester as a displacing agent to release sirolimus from endogenous binding substances in the sample. After conducting the assay, the resulting enzyme activity is measured and is related to the amount of both free sirolimus and sirolimus that was displaced from endogeneous binding substances. Subtraction of the enzyme activity obtained from the first sample portion from the enzyme activity obtained from the second sample portion gives the amount of enzyme activity attributed to the amount of sirolimus in the sample that was bound by endogeneous binding substances in the sample, which is related to the amount of bound sirolimus. The values may be used in the aforementioned equation to calculate a total amount of sirolimus in the sample in the presence of endogeneous interfering substances.

Measurement Step

Methods in accordance with the principles described herein wherein an immunoassay is used comprise examining each respective assay medium for the amount of a complex comprising the antibody for the analyte (anti-analyte antibody). The measurement is carried out respectively for each assay medium following the incubation of the assay medium in accordance with the particular assay employed. In the case of one sample portion, the measurement reflects an amount of free analyte in the sample (that is, analyte in the sample that is not bound by endogeneous binding substances) to anti-analyte antibody to form a complex comprising the anti-analyte antibody. In the case of a second sample portion, the measurement reflects an amount of analyte that represents the amount of analyte that is both free analyte in the samples as well as analyte in the sample that is released by addition of a displacing agent to anti-analyte antibody to form a complex comprising the anti-analyte antibody.

The phrase "measuring the amount of an analyte" refers to the quantitative, semi-quantitative and qualitative determination of the analyte. Methods that are quantitative, semi-quantitative and qualitative, as well as all other methods for determining the analyte, are considered to be methods of measuring the amount of the analyte. For example, a method, which merely detects the presence or absence of the analyte in a sample suspected of containing the analyte, is considered to be included within the scope of the present embodiments. The terms "detecting" and "determining," as well as other common synonyms for measuring, are contemplated within the scope of the present embodiments.

In many embodiments the examination of the medium involves detection of a signal from the medium. The amount of the signal is related to the amount of the analyte in the sample. The particular mode of detection depends on the nature of the signal producing system. As discussed herein, there are numerous methods by which a label of an sps can produce a signal detectable by external means, desirably by visual examination, and include, for example, electromagnetic radiation, electrochemistry, heat, radioactivity detection, and chemical reagents.

Activation of a signal producing system depends on the nature of the signal producing system members. For those members of a signal producing system that are activated with light, the member is irradiated with light. For members of signal producing systems that are on the surface of a particle, addition of a base may result in activation. Other activation methods will be suggested to those skilled in the art in view of the disclosures herein. For some signal producing systems, no agent for activation is necessary such as those systems that involve a label that is a radioactive label, an enzyme, and so forth. For enzyme systems, addition of a substrate and/or a cofactor may be necessary.

The examination for amount of the signal also includes the detection of the signal, which is generally merely a step in which the signal is read. The signal is normally read using an instrument, the nature of which depends on the nature of the signal. The instrument may be a spectrophotometer, fluorometer, absorption spectrometer, luminometer, chemiluminometer, actinometer, or a photographic instrument, for example. The amount of signal detected is related to the amount of the analyte present in a sample. Temperatures during measurements generally range from about 10° C. to about 70° C., or from about 20° C. to about 45° C., or about 20° C. to about 25° C., for example. In one approach standard curves are formed using known concentrations of the analytes to be screened. As discussed herein, calibrators and other controls may also be used.

Kits for Conducting Assays on the Sample Portions

The reagents for conducting a particular assay may be present in a kit useful for conveniently performing an assay for the determination of an analyte. In one embodiment a kit comprises in packaged combination reagents for displacing an analyte from endogenous binding substances, an antibody for an analyte and other reagents for performing an assay, the nature of which depend upon the particular assay format. The reagents may each be in separate containers or various reagents can be combined in one or more containers depending on the cross-reactivity and stability of the reagents. The kit can further include other separately packaged reagents for conducting an assay such as additional sbp members, ancillary reagents such as an ancillary enzyme substrate, and so forth.

The relative amounts of the various reagents in the kits can be varied widely to provide for concentrations of the reagents that substantially optimize the reactions that need to occur during the present method and further to optimize substantially the sensitivity of the assay. Under appropriate circumstances one or more of the reagents in the kit can be provided as a dry powder, usually lyophilized, including excipients, which on dissolution will provide for a reagent solution having the appropriate concentrations for performing a method or assay. The kit can further include a written description of a method in accordance with the present embodiments as described above.

Apparatus for Conducting Assays on the Sample Portions

As mentioned above, the methods in accordance with the principles described herein may be automated using an assay apparatus to carry out the method steps. The methods in accordance with the present invention may be carried out under computer control, that is, with the aid of a computer, which may be associated with the assay apparatus. The computer may be, for example, a personal computer (PC). The computer is driven by software that is particular for the methods described herein including the calculations using the aforementioned equations.

Software that may be used to carry out the methods may be, for example, Microsoft Excel or Microsoft Access, suitably extended via user-written functions and templates, and linked when necessary to stand-alone programs that perform other functions. Examples of software or computer programs used in assisting in conducting the present methods may be written in, for example, C, C++, or Visual basic. It should be understood that the above computer information and the software used herein are by way of example and not limitation. The present methods may be adapted to other computers and software.

A computer program may be utilized to carry out the above method steps. The computer program provides for (i) measuring an amount [Y] of a portion of the analyte in the unknown sample that is bound by endogenous binding substances employing an assay for the analyte, (ii) determining an amount [Z] of analyte in the unknown sample that is not bound by endogenous binding substances by the formula: [Z]=a[Y]+b, wherein "a" and "b" are predetermined by conducting the assay on samples containing known amounts of the analyte but substantially free from endogenous interfering substances, and (c) adding [Y] and [Z] to obtain the total amount [X] of the analyte in the unknown sample.

In some examples in accordance with the principles described, the computer program provides for (i) measuring an amount [Y] of a portion of tacrolimus that is bound by endogenous binding substances by (a') determining an amount [V] of tacrolimus by means of an assay conducted on a portion of the sample in the presence of an agent capable of displacing tacrolimus from endogenous binding substances, (b') determining an amount [W] of tacrolimus by means of an assay conducted on a portion of the sample in the absence of the agent capable of displacing tacrolimus from endogenous binding substances, and (c') subtracting [W] from [V], (ii) determining an amount [Z] of tacrolimus that is not bound by endogenous binding substances by the formula: [Z]=a[Y]+b, wherein "a" and "b" are predetermined by conducting the assay on samples containing known amounts of the analyte but substantially free from endogenous interfering substances, (c) adding [Y] and [Z] to determine a total amount [X] of tacrolimus in the sample.

The computer program may be carried on a program product that includes a computer readable storage medium having a computer program stored thereon and which, when loaded into a programmable processor, provides instructions to the processor of that apparatus such that it will execute the procedures required of it to perform a method of the present invention. The computer readable storage medium may be an optical, magnetic, or solid state memory, any of which may be portable or fixed. Some examples in accordance with the principles described herein are directed to a computer program product comprising a computer readable storage medium having a computer program stored thereon which, when loaded into a computer, performs the aforementioned method.

All publications and patent applications cited in this specification are herein incorporated by reference as if each individual publication or patent application were specifically and individually indicated to be incorporated by reference.

The phrase "at least" as used herein means that the number of specified items may be equal to or greater than the number recited. The phrase "about" as used herein means that the number recited may differ by plus or minus 10%; for example, "about 5" means a range of 4.5 to 5.5.

The following examples further describe the specific embodiments of the invention by way of illustration and not limitation and are intended to describe and not to limit the scope of the invention. Parts and percentages disclosed herein are by volume unless otherwise indicated.

EXAMPLES

All chemicals may be purchased from the Sigma-Aldrich Company (St. Louis Mo.) unless otherwise noted. Tacrolimus may be obtained from Astellas Pharma US. Inc., Deerfield Ill. Sirolimus may be obtained from Pfizer Inc., New York N.Y.

Testing is carried out using the DIMENSION® RxL analyzer, available from Siemens Healthcare Diagnostics Inc., Newark Del. The instrument is employed using ACMIA immunoassay technology. The ACMIA assay method is described in U.S. Pat. Nos. 7,186,518, 5,147,529, 5,128,103, 5,158,871, 4,661,408, 5,151,348, 5,302,532, 5,422,284, 5,447,870, and 5,434,051, the disclosures of which are incorporated herein in their entirety. In the embodiment of the ACMIA method used herein and discussed in more detail below, competition between tacrolimus analog on chrome particles and tacrolimus in patient samples for antibody for tacrolimus conjugated to an enzyme (the "conjugate") is utilized to determine the amount of tacrolimus in patient samples. Conjugate that binds to the tacrolimus analog on chrome particles is removed by magnetic separation. The enzymatic activity from conjugate remaining in the supernatant is measured and is directly proportional to the amount of tacrolimus in the patient sample. In the ACMIA assay format employed, the enzymatic activity observed when testing a sample containing no tacrolimus is indicative of the amount of enzymatic activity that is not bound to active antibody (i.e., cannot bind tacrolimus on chrome particles). The enzymatic activity observed when no chrome particle is present is indicative of the total amount of enzymatic activity in the conjugate. These values can be used to estimate the percent of enzymatic activity bound to active antibody.

Tacrolimus-free whole blood pools are screened by running the above mentioned ACMIA assay to identify whole blood pools that are substantially free from endogenous interfering substances. The screening is carried out by examining the consistency of tacrolimus recoveries of the pools to the individual tacrolimus-free whole blood samples. If the recoveries of the majority of the tacrolimus-free whole blood samples are within the low end sensitivity of the assay when the pool is used as the tacrolimus-free calibrator, the pool is accepted as a matrix free from endogenous interfering substances. The pool is then used to make the tacrolimus calibrators (or standards) by spiking different amounts of pure tacrolimus into the pool. The calibrators (which are substantially free from endogenous interfering substances) are then employed to generated the relationship of [Z]=a[Y]+b during the method calibration, which is achieved by testing the calibrators in the presence and absence of a displacing agent (sirolimus). Both [Z] and [Y] are generated from the calibration. The [Z] values of the calibrators are generated by running the calibrators in the absence of the displacing agent (representing the free drug) and the [Y] values of the calibrators are generated by subtracting the [Z] value from the total drug measured in the presence of the displacing agent (representing the bound drug). Calibrators made from a whole blood pool that is substantially free from endogeneous interfering substances are selected for use in the experiments below.

Example 1

Determination of Coefficients for Tacrolimus Assay Using Known Samples

Preparation of Anti-Tacrolimus Antibody-β-Galactosidase Conjugate.

Monoclonal anti-tacrolimus antibody (clone 1H6, see for example U.S. Pat. No. 7,078,495) is conjugated to β-galactosidase using a standard heterobifunctional SMCC (succinimidyl trans-4-(N-maleimidylmethyl)cyclohexane-1-carboxylate) linker according to known techniques. The antibody conjugate solution contains approximately 7.5 µg/mL anti-tacrolimus antibody-β-galactosidase conjugate, 30 mg/mL protease free bovine serum albumin, 0.126 mg/mL $MgCl_2$, 0.03 mL/mL of ethylene glycol, 35.14 mg/mL PIPES 1.5 sodium salt, 50 mg/mL NaCl and beta-gal mutein (inactivated β-galactosidase), pH 6.5.

Magnetic Chrome Particle Preparation.

Tacrolimus chrome particles (immunoassay solid phase) are prepared by conjugating tacrolimus-C22 oxime (prepared in a manner similar to that described in U.S. Pat. No. 7,078,495) to fluorescein, which is used to pre-decorate anti-fluorescein antibody immobilized on chromium dioxide particles through glutaraldehyde. The chrome particle reagent contains approximately 2.5 mg/mL tacrolimus chrome particle slurry, 60.8 mg/mL trehalose dihydrate and 7.2 mg/mL CARBOWAX®.

Preparation of Samples.

The whole blood pool substantially free from endogeneous interfering substances identified above is used. Aliquots (100 mL) of the whole blood pool are spiked with various amounts of tacrolimus so that the resulting concentration of tacrolimus in the whole blood samples is 0, 2.8, 6.0, 11.9 and 31.3 ng/mL (samples I-V).

Determination of Concentration of Free Tacrolimus Analyte Plus Bound Tacrolimus Analyte.

A set of samples I-V is treated as follows: To each sample is added a sirolimus (SIRO) displacing agent for displacing tacrolimus in the sample from endogeneous binding proteins. The formulation for the SIRO displacement solution is set forth in more detail in Table 1.

TABLE 1

| Name | Quantity (per mL) | Function |
| --- | --- | --- |
| SIRO | 5 µg/mL | Dissociating agent |
| SesquiNa PIPES | 17 mg/mL | buffer (pH 6.8) |
| EDTA Disodium | 0.75 mg/mL | Preventing clot formation |
| Saponin | 2.5 mg/mL | blood cell lysis |
| PROCLIN ® 300 | 5.0 ml/L | preservative |
| Neomycin sulfate | 0.06 gm/L | preservative |

The samples are incubated at 37° C. for a period of 140 minutes in the presence of displacing agent to displace tacrolimus from endogeneous binding substances. Subsequently, each sample is subjected to the aforementioned assay and signal (mAU) is measured and related to a concentration of analyte that represents the amount of free analyte (analyte that is not bound by endogenous binding substances plus analyte that was displaced from endogeneous binding substances) in the samples.

Assay.

The ACMIA assay for tacrolimus is as follows: 15 µL of a whole blood samples I-V from above (substantially free from endogeneous interfering substances and spiked with tacrolimus) is mixed with the SIRO displacement solution (Table 1) in a vessel on the DIMENSION® RxL analyzer. The whole blood is sampled from a standard cup by first mixing the blood with the ultrasonic sample probe. The mixing of whole blood sample with the SIRO displacement solution ensures the displacement of the bound tacrolimus molecules from their binding sites when the SIRO molecules are present. As a result, the signal generated from this assay is related to the amount of free tacrolimus analyte plus the amount of displaced tacrolimus analyte (bound analyte) in the sample.

Anti-tacrolimus antibody-β-galactosidase conjugate (50 µL) is added next to each of the reaction vessels and the mixture is held for a period of time (10 to 15 minutes) and at a temperature of 43° C. to allow tacrolimus, if present, to react with the antibody reagent. Chrome particles with immobilized tacrolimus-CM0-DA10-Dexal are added (50 µL) to each of the reaction vessels and are allowed to bind un-bound conjugate. The tacrolimus-bound anti-tacrolimus antibody-β-galactosidase conjugate does not bind to the chrome particles but remains in the supernatant when a magnetic field is applied to the above reaction mixtures to separate the solution from the chrome particles. The tacrolimus-bound conjugate is detected by transferring the supernatant from each of the reaction vessels to a photometric cuvette and measuring the enzymatic rate of the conjugate in the presence of chlorophenol red-β-D-galactopyranoside (CPRG). The rate for each reaction vessel is measured bichromatically at 577 and 700 nm.

Determination of Concentration of Free Tacrolimus Analyte.

A set of samples I-V is treated and assayed as above except that the formulation of Table 1 does not contain SIRO. As a result, the signal generated from this assay is for the amount of free tacrolimus analyte only in the sample.

Determination of Concentration of Bound Tacrolimus Analyte.

The concentration of bound tacrolimus analyte is determined by subtracting for each sample the concentration of free tacrolimus analyte from the concentration of free tacrolimus analyte plus bound tacrolimus analyte. The results are summarized in Table 2.

TABLE 2

| BV ng/mL | mAU + SIRO | mAU − SIRO | +SIRO ng/mL | −SIRO ng/mL | Protein-Bound ng/mL |
|---|---|---|---|---|---|
| 0.0 | 19 | 18 | 0.0 | 0.0 | 0.0 |
| 2.8 | 37 | 23 | 2.8 | 0.7 | 2.1 |
| 6.0 | 55 | 27 | 6.0 | 1.2 | 4.9 |
| 11.9 | 80 | 33 | 11.9 | 2.2 | 9.7 |
| 31.3 | 125 | 53 | 31.3 | 5.7 | 25.6 |

| Protein-Bound ng/mL | −SIRO ng/mL |
|---|---|
| 0.0 | 0.0 |
| 2.1 | 0.7 |
| 4.9 | 1.2 |
| 9.7 | 2.2 |
| 25.6 | 5.7 |
| Slope | 0.218 |
| Intercept | 0.0981 |

The concentration of free analyte is plotted against the concentration of bound analyte as shown in FIG. 1. The slope and intercept of the regression are 0.218 and 0.0981, respectively, which correspond to coefficients "a" and "b" in the formula $[Z]=a[Y]+b$, as discussed above.

The above ACMIA assay is then carried out on unknown samples known to contain endogenous interfering substances. Samples are obtained from various hospitals and are identified as set forth in first column of Table 3 below. The concentration of bound tacrolimus [Y] is determined as described above. The equation $[Z]=0.218[Y]+0.0981$ with the values for "a" and "b" determined as discussed above for this ACMIA assay is used to determine a concentration of free tacrolimus [Z] in the samples. The estimated true total concentration of tacrolimus [X] in each sample is determined by adding [Y]+[Z]. The results are summarized in Table 3.

TABLE 3

Estimated True values (ng/mL) for samples that show interference

| Sample | ng/mL + displacer | ng/mL − displacer | Bound drug | Free drug | Estimated True ng/mL |
|---|---|---|---|---|---|
| Dussel | 14.4 | 12.2 | 2.3 | 0.6 | 2.9 |
| 109 | 16.4 | 21.3 | 0.0 | 0.0 | 0.0 |
| FP15 | 10.9 | 3.8 | 7.1 | 1.6 | 8.7 |
| 864408 | 27.7 | 25.4 | 2.3 | 0.6 | 2.9 |
| 09-238-057 | 32.7 | 36.1 | 0.0 | 0.0 | 0.0 |

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Furthermore, the foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed. Many modifications and variations are possible in view of the above teachings. The embodiments were chosen and described in order to explain the principles of the invention and its practical applications and to thereby enable others skilled in the art to utilize the invention.

What is claimed is:

1. A method of determining a total amount of an analyte in an unknown sample suspected of containing the analyte in the presence of endogenous interfering substances, the method comprising:
    (a) measuring an amount [Y] of the analyte in the unknown sample that is bound by endogenous binding substances, wherein [Y] is measured by:
        (A) conducting an assay on a portion of the sample in the presence of a displacing agent wherein the assay comprises adding reagents for determining an amount of the analyte in the sample to a medium comprising the portion of the sample, wherein the reagents comprise at least one binding partner for the analyte, to determine an amount [V] of analyte in the sample that comprises both analyte bound by endogeneous binding substances and free analyte,
        (B) conducting the assay on another portion of the sample in the absence of a displacing agent to determine an amount [W] of free analyte in the sample, and
        (C) subtracting [W] from [V],
    (b) determining an amount [Z] of analyte in the unknown sample that is not bound by endogenous binding substances by the formula:

$[Z]=a[Y]+b,$ wherein "a" and "b" are predetermined by conducting the assay on samples containing known amounts of the analyte but substantially free from endogenous interfering substances, and
    (c) determining the total amount [X] of the analyte in the unknown sample by adding [Y] and [Z].

2. The method according to claim 1 wherein "a" is the slope of a regression between the analyte that is not bound by endogenous binding substances and analyte that is bound by endogenous binding substances, and "b" is the intercept of the regression.

3. The method of claim 1 wherein the sample is a body excretion, body aspirant, body excisant or body extractant.

4. The method according to claim 1 wherein the assay further comprises
    measuring in step (A) an amount of a complex comprising the binding partner for the analyte wherein the amount of the complex is related to the amount of the analyte in the sample and measuring in step (B) an amount of a complex comprising the binding partner for the analyte, wherein the amount of the complex is related to the amount of the analyte in the sample.

5. The method according to claim 1 wherein the reagents further comprise an analog of the analyte and the analog comprises a label.

6. The method according to claim 1 wherein the reagents further comprise a second binding partner wherein the second binding partner binds to a complex comprising the binding partner for the analyte.

7. The method according to claim 6 wherein at least the binding partner for the analyte or the second binding partner comprises a label.

8. The method according to claim 1 wherein one of the reagents comprises a label.

9. The method according to claim 1 wherein one of the reagents comprises a particle.

10. The method according to claim 1 wherein one of the reagents comprises an enzyme label and one of the reagents comprises a magnetic particle.

11. A method of determining a total amount of tacrolimus in a sample suspected of containing tacrolimus in the presence of endogenous interfering substances, the method comprising:
   (a) measuring an amount [Y] of tacrolimus that is bound by endogenous binding substances, wherein [Y] is measured by:
      (a') conducting an assay on a portion of the sample in the presence of an agent capable of displacing tacrolimus from endogenous binding substances to determine an amount [V] of tacrolimus,
      (b') conducting the assay on a portion of the sample in the absence of the agent capable of displacing tacrolimus from endogenous binding substances to determine an amount 1W1 of tacrolimus, and
      (c') subtracting [W] from [V]
   (b) determining an amount [Z] of tacrolimus that is not bound by endogenous binding substances by the formula:

$$[Z]=a[Y]+b,$$

wherein "a" and "b" are predetermined by conducting the assay on samples containing known amounts of the analyte but substantially free from endogenous interfering substances and wherein "a" is the slope of a regression between the analyte that is not bound by endogenous binding substances and analyte that is bound by endogenous binding substances, and "b" is the intercept of the regression, and
   (c) determining the total amount [X] of tacrolimus by adding [Y] and [Z].

12. The method of claim 11 wherein the sample is a body excretion, body aspirant, body excisant or body extractant.

13. The method according to claim 11 wherein the assay method is a homogeneous assay method.

14. The method according to claim 11 wherein the assay comprises:
   (i) adding reagents for determining an amount of tacrolimus in the sample to a medium comprising the portion of the sample of step (a') and to a medium comprising the portion of the sample of step (b') wherein the reagents comprise at least one binding partner for tacrolimus, and
   (ii) measuring in step (a') an amount of a complex comprising the binding partner for tacrolimus wherein the amount of the complex is related to the amount of tacrolimus in the sample and measuring in step (b') an amount of a complex comprising the binding partner for tacrolimus, wherein the amount of the complex is related to the amount of tacrolimus in the sample.

15. The method according to claim 14 wherein the reagents in step (i) further comprise an analog of tacrolimus and the antibody for tacrolimus or the analog comprises a label.

16. The method according to claim 14 wherein in step (i) a second antibody is added to the medium wherein the second antibody binds to a complex comprising the antibody for tacrolimus.

17. The method according to claim 16 wherein the antibody for tacrolimus or the second antibody comprises a label.

18. The method according to claim 14 wherein one of the reagents comprises a label.

19. The method according to claim 14 wherein one of the reagents comprises a particle.

20. The method according to claim 14 wherein one of the reagents comprises an enzyme label and one of the reagents comprises a magnetic particle.

* * * * *